(12) United States Patent
Somma et al.

(10) Patent No.: US 10,654,081 B2
(45) Date of Patent: May 19, 2020

(54) STERILIZING APPARATUS, IN PARTICULAR FOR STERILIZING POST-CONSUMER ABSORBENT SANITARY PRODUCTS

(71) Applicant: FATER S.p.A., Pescara (IT)

(72) Inventors: Marcello Somma, Pescara (IT); Giorgio Vaccaro, Pescara (IT); Amedeo Pagotto, Pescara (IT)

(73) Assignee: FATER S.P.A., Pescara (IT)

( * ) Notice: Subject to any disclaimer, the term of this patent is extended or adjusted under 35 U.S.C. 154(b) by 0 days.

(21) Appl. No.: 16/038,951

(22) Filed: Jul. 18, 2018

(65) Prior Publication Data

US 2019/0070648 A1 Mar. 7, 2019

(30) Foreign Application Priority Data

Sep. 6, 2017 (IT) .......................... 102017000099949

(51) Int. Cl.
*B09B 3/00* (2006.01)
*A61L 2/07* (2006.01)
*A61L 11/00* (2006.01)
*B29L 31/48* (2006.01)

(52) U.S. Cl.
CPC .............. *B09B 3/0091* (2013.01); *A61L 2/07* (2013.01); *A61L 11/00* (2013.01); *B09B 3/0075* (2013.01); *B09B 3/0083* (2013.01); *A61L 2202/122* (2013.01); *B01J 2219/00081* (2013.01); *B29L 2031/4878* (2013.01)

(58) Field of Classification Search
CPC ... B09B 3/0091; B09B 3/0083; B09B 3/0075; B01J 2219/00081; A61L 11/00; A61L 2/07; A61L 2202/122
See application file for complete search history.

(56) References Cited

U.S. PATENT DOCUMENTS

| 2,848,198 | A | | 8/1958 | Bill |
| 6,071,474 | A | * | 6/2000 | Martinsen ............... A23L 3/165 422/26 |
| 6,171,261 | B1 | * | 1/2001 | Niermann .......... A61B 10/0096 600/573 |

(Continued)

FOREIGN PATENT DOCUMENTS

| EP | 0923318 B1 | 4/2002 |
| EP | 2596810 A1 | 5/2013 |
| WO | 2010065088 A1 | 6/2010 |

OTHER PUBLICATIONS

Italian Search Report and Written Opinion dated May 9, 2018 for Application No. IT102017000099949.

*Primary Examiner* — Sean E Conley
*Assistant Examiner* — Brendan A Hensel
(74) *Attorney, Agent, or Firm* — Patterson + Sheridan, LLP

(57) ABSTRACT

A sterilizing apparatus, in particular for sterilizing post-consumer absorbent sanitary products, comprising: a container rotatable about a horizontal axis and having a hollow wall including an inner wall, an outer wall, and a gap defined between the inner wall and the outer wall, a rotary joint coaxial to said horizontal axis and having a steam inlet chamber and a condensate discharge chamber, wherein the steam inlet chamber and the condensate discharge chamber of said rotary joint are in communication with respective zones of said gap via a steam supply tube and a condensate collection tube.

4 Claims, 4 Drawing Sheets

(56) References Cited

U.S. PATENT DOCUMENTS

2009/0007484 A1\* 1/2009 Smith ................ C10B 47/44
  44/606
2016/0242454 A1 8/2016 Waeny \* cited by examiner

STERILIZING APPARATUS, IN PARTICULAR FOR STERILIZING POST-CONSUMER ABSORBENT SANITARY PRODUCTS

CROSS-REFERENCE TO RELATED APPLICATIONS

This application claims benefit of Italian patent application number 102017000099949, filed Sep. 6, 2017 which is herein incorporated by reference.

BACKGROUND OF THE INVENTION

Field of the Invention

The present invention relates to a sterilizing apparatus, in particular for sterilizing post-consumer absorbent sanitary products.

The term "absorbent sanitary products" generally refers to disposable absorbent products, such as diapers for babies, incontinence pads for adults, sanitary towels, absorbent tampons, absorbent bed linings, etc.

Description of Prior Art

Absorbent sanitary products are generally composed of a variety of different materials, including sheets of plastic material, cellulose fluff, superabsorbent polymers, non-woven sheets, etc.

Absorbent sanitary products contain high-quality materials such as plastics and cellulose and it is, therefore, desirable to recover these materials for use in the market of recycled raw materials or for producing energy.

One of the difficulties encountered in the recycling of post-consumer absorbent sanitary products is that these products contain organic excretions and bacteria and it is therefore necessary to sterilize the products before separating the materials. An additional difficulty derives from the fact that used absorbent sanitary products are usually discarded folded on themselves as a package, with the outer plastic layer of the products forming an impermeable barrier. The outer waterproof layer prevents effective sterilization of the products.

The document WO 2010/065088 describes an autoclave for treating solid urban waste, which envisages the drying of the waste by steam. The apparatus described in the document WO 2010/065088 comprises a cylindrical rotating autoclave equipped with at least one door, which can be opened to allow access inside the autoclave, and sealed closed to allow pressurization of the autoclave; an inlet for contact steam that comes into direct contact with the waste contained within the autoclave; and a plurality of hollow metal bars with a rectangular cross-section fed with non-contact steam. This apparatus allows the sterilization of urban solid waste and the drying of the waste during autoclaving.

EP-A-2596810 by the same applicant describes a method for treating used absorbent sanitary products, which envisages: loading post-consumer absorbent sanitary products into a cylindrical rotating autoclave having an inner surface, then heating and pressurizing the autoclave at a sterilization temperature and—at the same time—rotating the autoclave about a longitudinal axis thereof. For heating the autoclave, contact steam is supplied in direct contact with the absorbent sanitary products contained in the autoclave, and non-contact steam that heats the autoclave wall.

The heat required for reaching the temperature for sterilizing the products contained in the autoclave comes mostly from the heat energy transferred through the inner wall of the autoclave. One of the problems encountered for heating the autoclave wall is extracting the condensed steam. The non-contact steam that condenses in the autoclave wall tends to deposit in the lower part of the autoclave and can cause a reduction in the volume available for the steam, thereby reducing the exchange surface between the steam and the autoclave wall. If the heat exchange between the wall of the autoclave and the absorbent sanitary products is not optimal, with the same thermal energy available, the transfer time of the thermal energy to the products is high, and consequently the time of the sterilization cycle of the products is high.

SUMMARY OF THE INVENTION

The object of the present invention is to provide an apparatus for sterilizing post-consumer absorbent sanitary products that allows optimization of the transfer of thermal energy from the walls of the apparatus to the products.

According to the present invention, this object is achieved by an apparatus having the features disclosed herein.

BRIEF DESCRIPTION OF THE DRAWINGS

The present invention will now be described in detail with reference to the attached drawings, given purely by way of non-limiting example, wherein.

It will be appreciated that, for clarity and simplicity of illustration, the various figures may not be reproduced on the same scale.

DETAILED DESCRIPTION

Figure 1:
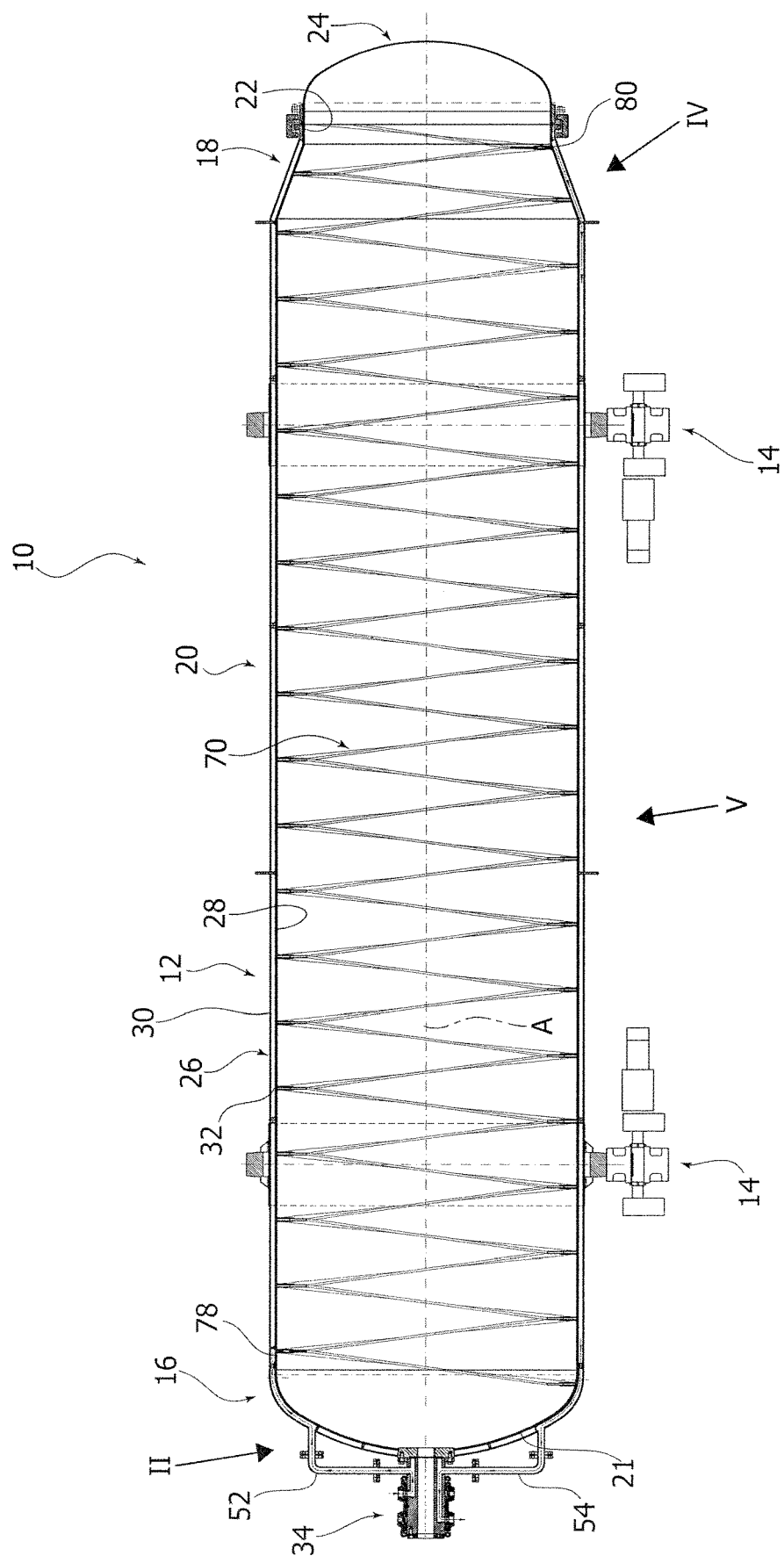
FIG. 1 is an axial cross-section of an apparatus according to the present invention.

With reference to FIG. 1, numeral 10 indicates an apparatus for sterilizing post-consumer absorbent sanitary products.

The apparatus 10 comprises a container 12 rotatably supported about a longitudinal axis A by means of stationary supports 14, at least one of which is provided with actuating means that rotate the container 12 about the axis A. The longitudinal axis A of the container 12 is fixed, preferably in a horizontal position.

The container 12 comprises a cylindrical body 20 elongated along the longitudinal axis A, which extends between a first end 16 and a second end 18. The first end 16 of the cylindrical body 20 is closed by a rounded portion 21 with a generally hemispherical shape, and the second end 18 is provided with a loading/unloading opening 22, which is sealed closed by a removable door 24.

The container 12 has a hollow wall 26 including an inner wall 28 and an outer wall 30 that enclose a gap 32. The gap 32 extends along the entire cylindrical body 20, from the first end 16 to the second end 18. The gap 32 can also be extended onto the rounded portion 21. The inner wall 28 of the container 12 delimits a treatment volume of the products. The outer surface of the outer wall 30 of the container 26 may be covered by an isolating layer 85.

Figure 2:
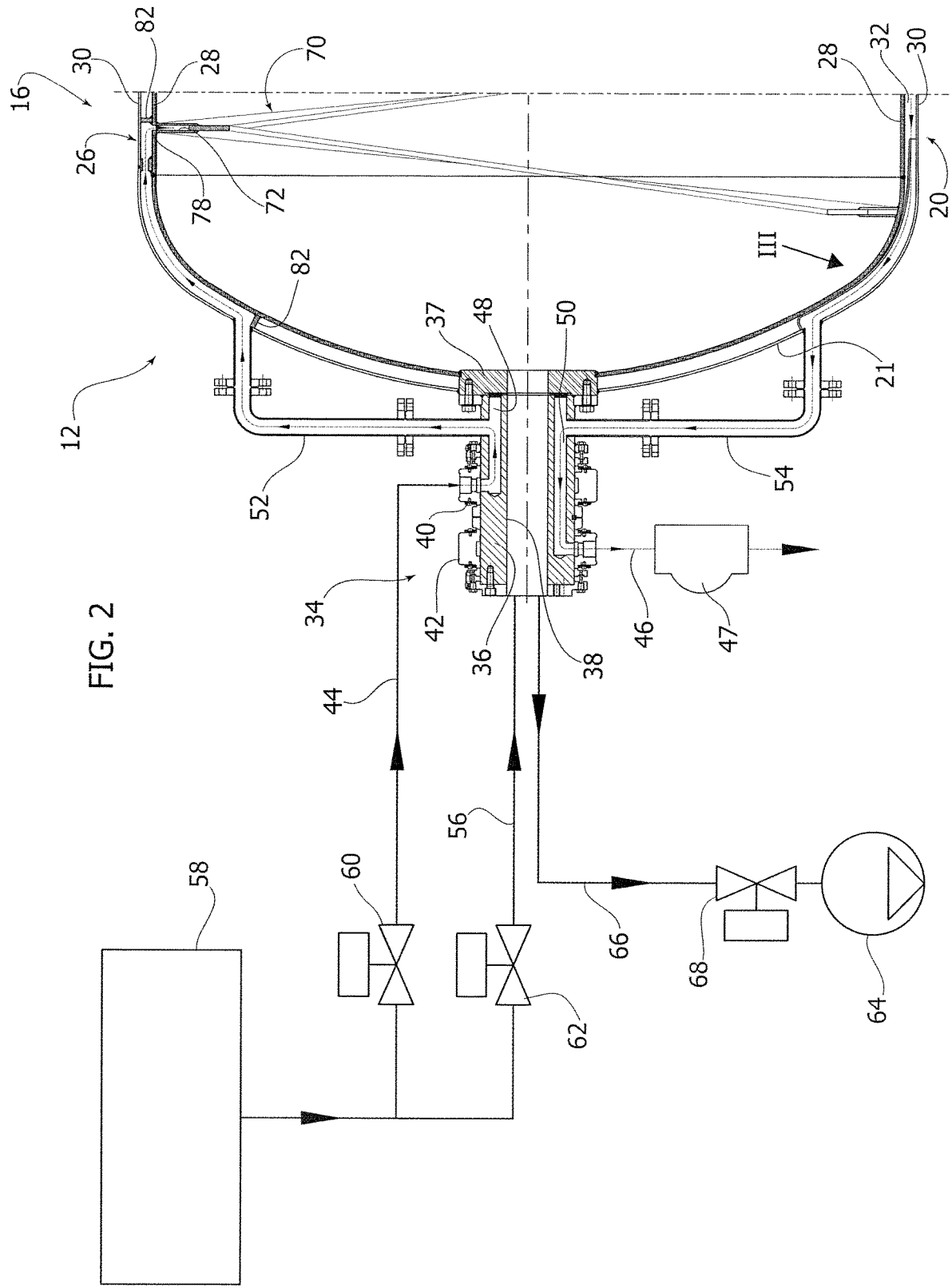
FIG. 2 is a schematic view on an enlarged scale of the part indicated by the arrow II in FIG. 1.

With reference to FIG. 2, the container 12 comprises a rotary joint 34 coaxial with the longitudinal axis A. The rotary joint 34 is fixed to the rounded portion 21 of the container 12. The rotary joint 34 comprises a hub 36 fixed by means of a flange 37 to the wall 26 of the container 12. The hub 36 has a central hole 38 in communication with the inside of the container 12.

The rotary joint 34 comprises two stationary rings 40, 42 in sliding sealed contact with the central hub 36. The stationary rings 40, 42 are connected, respectively, to a first steam supply tube 44 and to a condensate discharge tube 46. An automatic condensate discharge device 47 is arranged on the condensate discharge tube 46.

In the central hub 36, a steam supply chamber 48 and a condensate discharge chamber 50 are formed, in fluid connection with the respective stationary rings 40, 42. The steam supply chamber 48 and the condensate discharge chamber 50 are connected to separate zones of the gap 32 by means of a steam supply tube 52 and a condensate collection tube 54.

The central hole 38 of the hub 36 is connected to a second steam supply tube 56, which supplies pressurized steam inside the container 12 in direct contact with the products (contact steam). The steam supply tubes 44, 56 are connected to a steam generator 58 by means of respective valves 60, 62. The central hole 38 of the hub 36 can also be connected to a vacuum pump 64 via an intake tube 66 and a valve 68. The vacuum pump 64 can extract air from inside the container 12 before carrying out the pressurization of the container 12 with the contact steam coming from the second steam supply tube 56.

With reference to FIG. 1, the container 12 may have at least one hollow helical blade 70 fixed to the inner wall 28 of the container 12 and projecting inwardly in the container 12. The hollow helical blade 70 may form a screw coaxial with the longitudinal axis A. The hollow helical blade can extend in the longitudinal direction A between the first end 16 and the second end 18 of the container 12.

Figure 3:
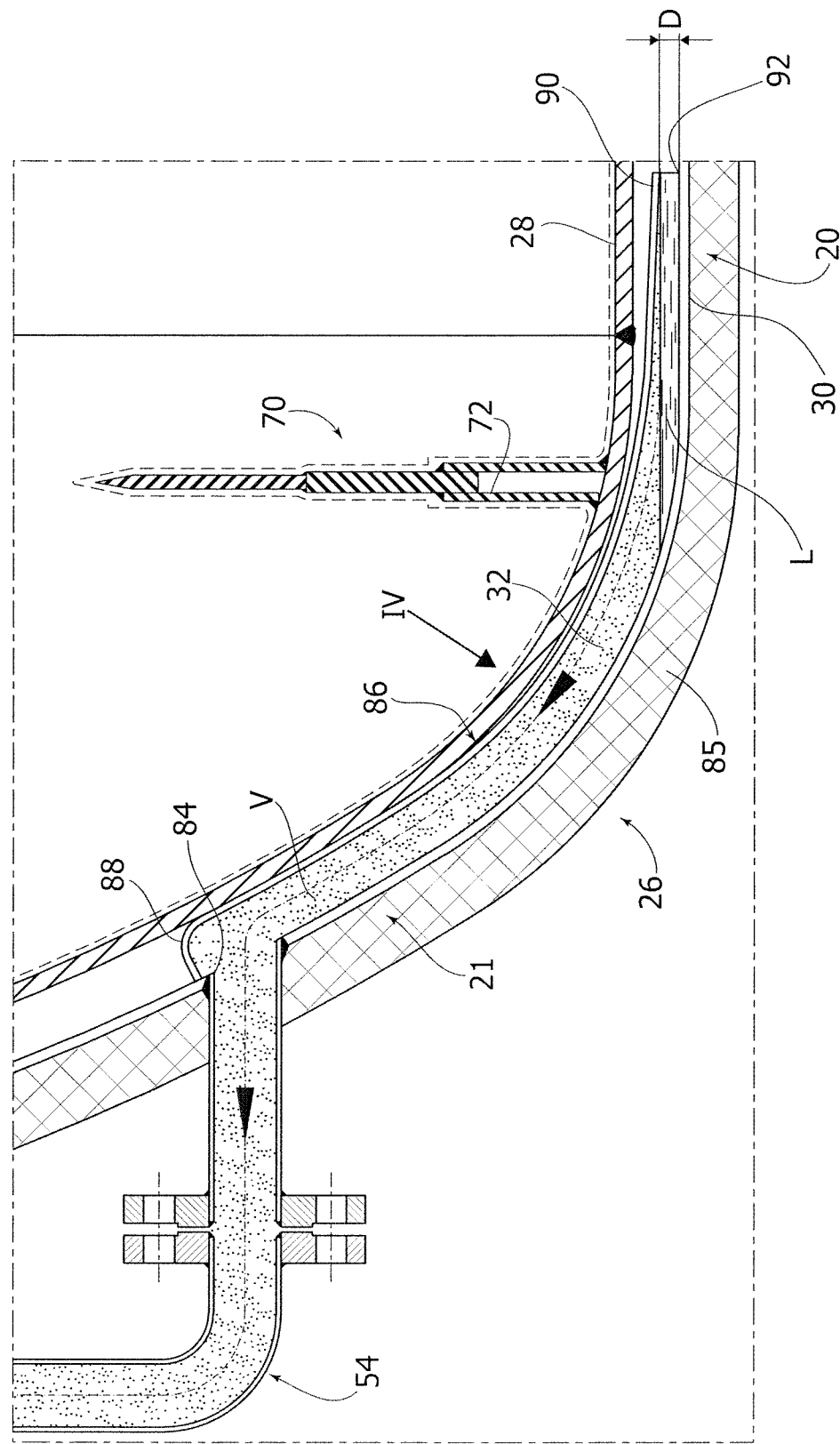
FIG. 3 is an enlarged cross-section of the detail indicated by the arrow III in FIG. 2.

With reference to FIGS. 2 and 3, the hollow helical blade 70 has a cavity 72 that extends along the entire length of the hollow helical blade 70. With reference to FIG. 1, the helical cavity 72 has an inlet opening 78 in communication with the gap 32 in the first end 16 of the container 12 and an outlet opening 80 in communication with the gap 32 in the second end 18 of the container 12. The helical cavity 72 of the helical blade 70 only communicates with the gap 32 through the inlet opening 78 and the outlet opening 80. Between the inlet opening 78 and the outlet opening 80, the helical cavity 72 is isolated from the gap 32.

With reference to FIG. 2, the portion of the gap 32 between the outlet of the first steam supply tube 52 and the inlet opening 78 of the helical cavity 72 is sealed closed by septa 82, so that the inlet opening 78 is isolated from the remaining part of the gap 32, and communicates with the steam supply chamber 48 of the rotating connector 34 through a portion of the gap 32 and through the steam supply tube 52. Alternatively, the outlet of the tube 52 could be directly connected to the inlet opening 78 of the helical cavity 72 without a gap portion between the outlet of the tube 52 and the inlet opening 78.

Figure 4:
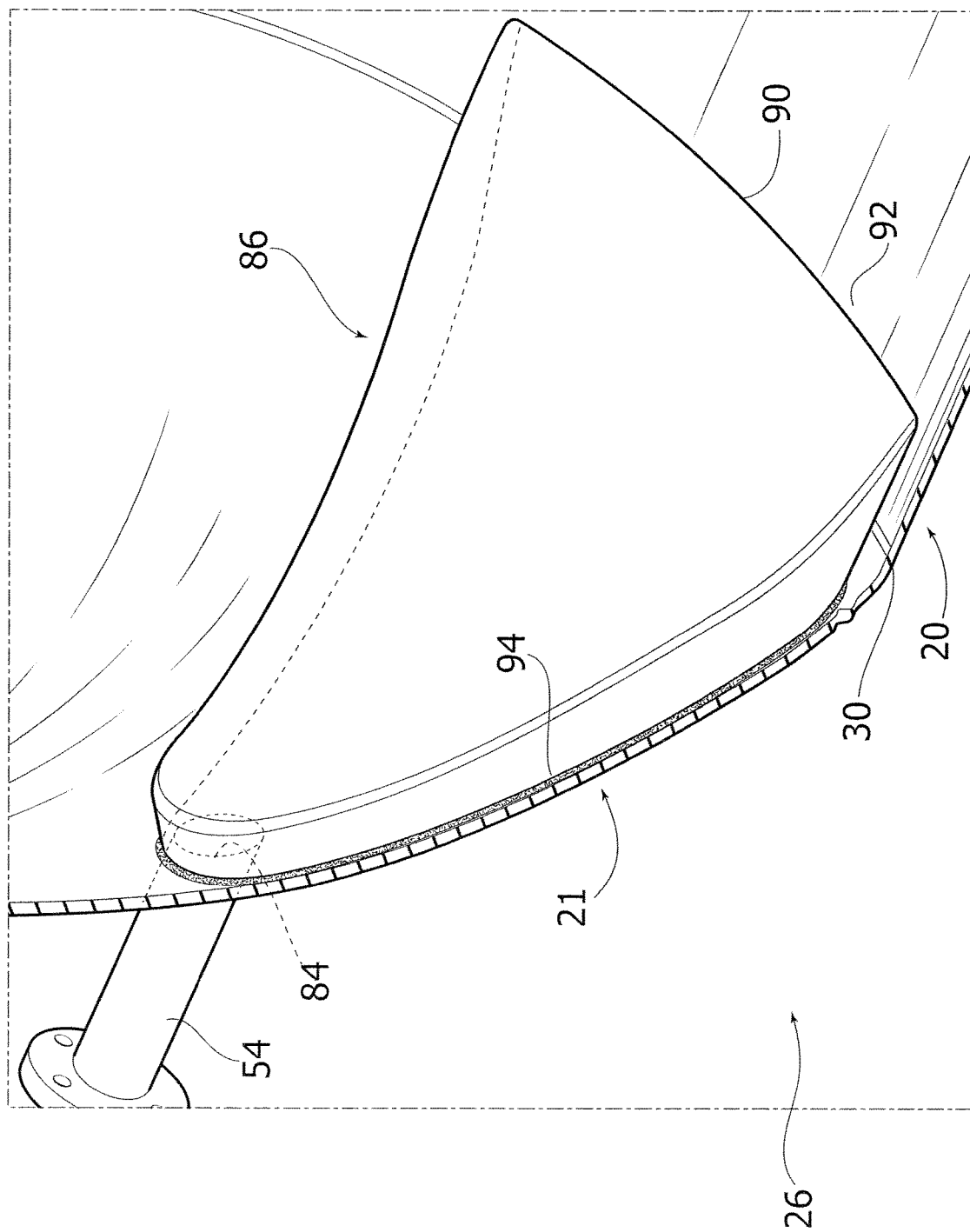
FIG. 4 is a perspective view of the part indicated by the arrow IV in FIG. 3.

With reference to FIGS. 3 and 4, the condensate collection tube 54 has a condensate inlet end 84 attached to the outer wall 30 of the container 26 at the hemispherical rounded portion 21. The condensate inlet end 84 of the condensate collection tube 54 communicates with the gap 32 inside the first end 16 of the container 12.

With reference to FIGS. 3 and 4, the container 26 comprises a condensate collection container 86 attached to the container 12 inside the gap 32. The condensate collection container 86 may be formed by a shaped metal sheet adjacent to the inner wall 28 of the container 12.

The condensate collection container 86 has a first end 88 closed around the condensate inlet end 84 of the condensate collection tube 54 and a second end provided with a lip 90 facing a cylindrical portion 92 of the outer wall 30 of the container 12.

The lip 90 is open in the gap 32 and is elongated in a circumferential direction. The lip 90 is located at a distance D from the outer wall 30, which can be between 5 and 15 mm.

The side edges of the condensate collection container 86 are attached to the outer wall 30 by a weld 94. The condensate collection container 86 forms a chamber that is only open in the gap 32 at the lip 90. The condensate collection container 86 allows direct communication of the condensate inlet end 84 of the condensate collection tube 54 with the gap 32 at the lip 90.

The condensate collected in the gap 32 can enter the condensate collection container 86 through the lip 90 when the condensate collection container 86 reaches the lowest position during rotation of the container 12 about the axis A. The shape of the condensate collection container 86 from the first end 88 to the second end allows the condensate to remain inside the condensate collection container 86 during rotation of the container 12 and then to drop by gravity into the condensate inlet end 84 of the condensate collection tube 54 when the condensate collection container 86 reaches the highest position during rotation of the container 12.

In operation, the container 12 is loaded with a load of post-consumer absorbent sanitary products coming from the recycling collection. Then, the treatment volume is filled with pressurized contact steam fed through the hole 38 of the rotary joint 34. At the same time, the container 12 is rotated about the longitudinal axis A.

The wall 26 of the container 12 and the hollow helical blade 70 are heated by non-contact steam. The non-contact steam is supplied by the chamber 48 of the rotary joint 34 to the inlet opening 78 of the hollow helical blade 70. Non-contact steam travels through the helical cavity 72 of the hollow helical blade 70. At the outlet 80 of the helical cavity 72, the non-contact steam fills the gap 32 of the wall 26. The non-contact steam first crosses the helical blade 70 and subsequently travels across the gap 32 from the second end 18 towards the first end 16.

In operation, the gap 32 and the condensate collection tube 54 are filled with steam, indicated by V in FIG. 3. The steam V is confined within the condensate collection tube 54 and the gap 32, without the possibility of exiting. In fact, the automatic condensate discharger 47, connected to the condensate collection tube 54, by means of the rotary joint 34, prevents outlet of steam V. The automatic condensate discharger 47 only allows the outlet of liquids (condensed steam).

The liquid that is formed by the condensation of the steam V inside the gap 32 is indicated by L in FIG. 3. The liquid L is collected by gravity on the bottom of the gap 32 and forms a layer of liquid adhering to the outer wall 30 that always remains in the lowest position of the gap 32.

During rotation of the container 12 about the axis A, the condensate collection container 86 comes into contact cyclically with the liquid L when it passes into the lowest position during rotation of the container 26. When the condensate collection container 86 comes into contact with the liquid L, the liquid L enters the condensate collection container 86 through the lip 90. During the return of the condensate collection container 86, the liquid L that had previously entered through the lip 90 remains inside the condensate collection container 86. When the condensate collection container 86 reaches the highest point during rotation of the container 26, the liquid L contained in the condensate collection container 86 falls by gravity towards the condensate inlet end 84 of the condensate collection tube 54. The liquid L progressively fills the condensate collection tube 54 and is expelled through the condensate collection tube 54, the rotary joint 34, the condensate discharge tube 46 and the automatic condensate discharge device 47.

The condensate collection container 86 maintains the level of liquid L in the gap 32 below the distance D between the lip 90 and the outer wall 30. In this way, the problem of filling the gap 32 with the liquid L coming from the condensation of the non-contact steam is effectively prevented. A reduction of the heat exchange surface between the steam and the inner wall 28 of the container 26 is therefore avoided.

Of course, without prejudice to the principle of the invention, the details of construction and the embodiments may be widely varied, without thereby departing from the scope of the invention as defined by the claims that follow.

| LIST OF REFERENCE SIGNS | |
|---|---|
| apparatus | 10 |
| container | 12 |
| longitudinal axis | A |
| stationary supports | 14 |
| cylindrical body | 20 |
| first end | 16 |
| second end | 18 |
| rounded portion | 21 |
| opening | 22 |
| removable door | 24 |
| hollow wall | 26 |
| inner wall | 28 |
| outer wall | 30 |
| gap | 32 |
| rotary joint | 34 |
| hub | 36 |
| flange | 37 |
| central hole | 38 |
| stationary rings | 40, 42 |
| first steam supply tube | 44 |
| condensate discharge tube | 46 |
| automatic condensate discharge device | 47 |
| steam supply chamber | 48 |
| condensate discharge chamber | 50 |
| steam supply tube | 52 |
| condensate collection tube | 54 |
| second steam supply tube | 56 |
| steam generator | 58 |
| valves | 60, 62 |
| vacuum pump | 64 |
| intake tube | 66 |
| valve | 68 |
| hollow helical blade | 70 |
| cavity | 72 |
| inlet opening | 78 |
| outlet opening | 80 |
| septa | 82 |
| condensate inlet end | 84 |
| isolating layer | 85 |
| condensate collection container | 86 |
| first end | 88 |
| cylindrical portion | 92 |
| weld | 94 |

The invention claimed is:

1. A sterilizing apparatus for sterilizing post-consumer absorbent sanitary products, comprising:
   a main container rotatable about a horizontal axis, and having a hollow wall including an inner wall, an outer wall, and a gap defined between the inner wall and the outer wall,
   a rotary joint coaxial to the horizontal axis and having a steam inlet chamber and a condensate discharge chamber, wherein the steam inlet chamber and the condensate discharge chamber of the rotary joint are in communication with respective zones of the gap via a steam supply tube and a condensate collection tube, wherein the condensate collection tube has a condensate inlet end attached to the outer wall of the container and is in fluid communication with the gap; and
   a condensate collection container fixed to the main container inside the gap, wherein:
      the condensate collection container extends from a first end closed around the condensate inlet end of the condensate collection tube to a second open end provided with a lip open in the gap and elongated in a circumferential direction of a cylindrical portion of the outer wall, the elongated lip being curved with a radius having a center in common with a center of the cylindrical portion of the outer wall,
      when the condensate collection container reaches a lowest position relative to the horizontal axis during rotation of the main container, condensate that has collected in a cylindrical portion of the gap enters into the condensate collection container through the elongated lip, and
      when the condensate collection container reaches a highest position relative to the horizontal axis during rotation of the main container, condensate that has entered the condensate collection container through the elongated lip and that remains within the condensate collection container during rotation of the main container then falls off by gravity into the condensate inlet end of the condensate collection tube.

2. The sterilizing apparatus according to claim 1, wherein the elongated lip of the condensate collection container is located at a distance from the outer wall of the main container of between 5 and 15 mm.

3. The sterilizing apparatus according to claim 1, wherein at least one side edge of the condensate collection container is attached to the outer wall by a weld.

4. The sterilizing apparatus according to claim 2, wherein the elongated lip is shaped and positioned so that, when the condensate collection container reaches a lowest position relative to the horizontal axis during rotation of the main container, condensate that has collected in the cylindrical portion of the gap above the distance from the outer wall enters into the condensate collection container through the elongated lip, and condensate that has collected in the cylindrical portion of the gap below the distance from the outer wall remains in the gap.

\* \* \* \* \*